(12) United States Patent
Hogle

(10) Patent No.: US 7,108,706 B2
(45) Date of Patent: Sep. 19, 2006

(54) INFLATABLE NASAL PACKING DEVICE WITH TWO NON-ELASTIC, FLEXIBLE BAGS OVERSIZED RELATIVE TO NASAL CAVITIES

(75) Inventor: Gregory A. Hogle, Denver, CO (US)

(73) Assignee: Rose Biomedical Development Corporation, Denver, CO (US)

( * ) Notice: Subject to any disclaimer, the term of this patent is extended or adjusted under 35 U.S.C. 154(b) by 152 days.

(21) Appl. No.: 10/447,179

(22) Filed: May 28, 2003

(65) Prior Publication Data

US 2004/0243172 A1 Dec. 2, 2004

(51) Int. Cl.
*A61M 29/00* (2006.01)
(52) U.S. Cl. .................................. 606/199; 604/358
(58) Field of Classification Search ................ 606/127, 606/150–154, 196, 199; 604/94, 101, 286, 604/101.01, 101.02, 101.05, 358; 128/207.18
See application file for complete search history.

(56) References Cited

U.S. PATENT DOCUMENTS

| | | | |
|---|---|---|---|
| 3,570,494 A | 3/1971 | Gottschalk | |
| 3,766,924 A | 10/1973 | Pidgeon | |
| 3,850,176 A | 11/1974 | Gottschalk | |
| 3,903,893 A * | 9/1975 | Scheer | 606/196 |
| 4,182,342 A * | 1/1980 | Smith | 604/172 |
| 4,457,756 A | 7/1984 | Kern et al. | |
| 4,568,326 A | 2/1986 | Rangaswamy | |
| 4,646,739 A | 3/1987 | Doyle | |
| 4,820,266 A | 4/1989 | Berry | |
| 4,883,465 A | 11/1989 | Brennan | |
| 4,938,234 A | 7/1990 | Capriotti | |
| 4,950,280 A | 8/1990 | Brennan | |
| 5,011,474 A | 4/1991 | Brennan | |
| 5,024,658 A | 6/1991 | Kozlov et al. | |
| 5,112,353 A | 5/1992 | Johansson | |
| 5,114,399 A | 5/1992 | Kovalcheck | |
| 5,139,510 A | 8/1992 | Goldsmith, III et al. | |
| 5,284,469 A | 2/1994 | Jasen et al. | |
| 5,336,163 A | 8/1994 | DeMane et al. | |
| 5,362,303 A | 11/1994 | Jasen et al. | |
| 5,383,891 A | 1/1995 | Walker | |
| 5,391,179 A | 2/1995 | Mezzoli | |
| 5,496,303 A * | 3/1996 | Antonetti | 604/410 |
| 5,496,345 A | 3/1996 | Kieturakis et al. | |
| 5,546,964 A | 8/1996 | Stangerup | |

(Continued)

FOREIGN PATENT DOCUMENTS

DE    DT 23 32 554 A1    1/1975

(Continued)

*Primary Examiner*—Gary Jackson
*Assistant Examiner*—Victor Nguyen
(74) *Attorney, Agent, or Firm*—Townsend and Townsend and Crew LLP

(57) ABSTRACT

An inflatable nasal packing device, and method of use, for insertion in a patient's nasal cavity to control bleeding or epistaxis. The device includes a flexible insertion tube, a first inflatable bag attached to and surrounding an anterior section of the tube, and a second inflatable bag attached to and surrounding a posterior section of the tube. The tube has three lumens for providing separate fill passageways to the two bags to allow independent filling and pressurization and for providing an air passageway through the device even when the bags are inflated. Both bags have walls of non-elastic, flexible material with fixed surface areas defining interior volumes when inflated that are larger than the anterior nasal cavity and the posterior nasal cavity and nasopharynx.

16 Claims, 7 Drawing Sheets

U.S. PATENT DOCUMENTS

| | | | |
|---|---|---|---|
| 5,584,822 A | 12/1996 | Lively et al. | |
| 5,584,827 A | 12/1996 | Korteweg et al. | |
| 5,584,871 A | 12/1996 | Mosley | |
| 5,700,252 A | 12/1997 | Klingenstein | |
| 5,755,706 A | 5/1998 | Kronenthal et al. | |
| D406,888 S | 3/1999 | Doyle | |
| D406,890 S | 3/1999 | Doyle | |
| 5,913,872 A | 6/1999 | Suh et al. | |
| 6,169,123 B1 | 1/2001 | Cercone | |
| 6,183,436 B1 | 2/2001 | Korteweg et al. | |
| 6,214,895 B1 | 4/2001 | Cercone | |
| 6,306,154 B1 | 10/2001 | Hudson et al. | |
| 6,328,753 B1 * | 12/2001 | Zammit | 606/196 |
| 6,450,986 B1 | 9/2002 | Binner et al. | |
| 6,607,546 B1 * | 8/2003 | Murken | 606/196 |
| 6,706,051 B1 | 3/2004 | Hudson et al. | |
| 6,768,040 B1 | 7/2004 | Sessions et al. | |
| 2002/0058960 A1 | 5/2002 | Hudson et al. | |
| 2002/0077653 A1 | 6/2002 | Hudson et al. | |
| 2002/0087166 A1 | 7/2002 | Brock et al. | |
| 2002/0087169 A1 | 7/2002 | Brock et al. | |
| 2002/0095175 A1 | 7/2002 | Brock et al. | |
| 2003/0097099 A1 | 5/2003 | Quinn | |
| 2003/0105462 A1 | 6/2003 | Hudson et al. | |
| 2003/0105469 A1 | 6/2003 | Karmon | |
| 2003/0105483 A1 | 6/2003 | Hudson et al. | |
| 2003/0163062 A1 | 8/2003 | Bauer | |
| 2003/0233095 A1 | 12/2003 | Urbanski et al. | |
| 2003/0236547 A2 | 12/2003 | Hudson et al. | |
| 2004/0073299 A1 | 4/2004 | Hudson et al. | |
| 2004/0194788 A1 | 10/2004 | Sweal | |

FOREIGN PATENT DOCUMENTS

| | | | |
|---|---|---|---|
| GB | 2 261 819 A | 6/1993 | |
| SE | 220978 | 6/1968 | |
| WO | WO 96/39218 | * 12/1996 | 606/199 |

* cited by examiner

INFLATABLE NASAL PACKING DEVICE WITH TWO NON-ELASTIC, FLEXIBLE BAGS OVERSIZED RELATIVE TO NASAL CAVITIES

REFERENCE TO RELATED APPLICATIONS

This application is related to U.S. application Ser. No. 08/466,382, filed Jun. 6, 1995, now abandoned, and U.S. application Ser. No. 08/867,983, filed Jun. 3, 1997, now abandoned.

BACKGROUND OF THE INVENTION

1. Field of the Invention

The present invention relates generally to the field of nasal packing devices, and more particularly, to a nasal packing device that includes an anterior and a posterior bag on a structural tube to allow insertion into a patient's nasal cavity. The two bags are fabricated from a relatively inelastic material, are oversized to provide a fixed surface area that defines a bag volume that is larger than the nasal cavity volume, and are independently inflatable via lumens in the structural tube initially at a relatively low fill pressure to cause the bags to fill slowly to contact all or most of the nasal cavity surfaces and then once positioned and shaped at a higher contact or force-applying pressure to stop anterior and/or posterior epistaxis (e.g., using pressures directly contrasting with balloon inflation which requires high initial pressures to initiate elastic material stretching).

2. Relevant Background

Physicians are frequently called upon to treat nasal bleeding, i.e., epistaxis, that can be caused by tissue desiccation, trauma, disease, or surgical procedures. Epistaxis can produce rapid, extensive blood loss because of the extensive blood supply to the nose, and in some cases, blood transfusion may be required to treat the patient. Due to the seriousness of some cases of epistaxis, the physician's first concern is to control the bleeding as quickly as possible. The physician needs to be able to efficiently and accurately insert the nasal packing or nasal packing device into the correct position and to then use the packing or operate the device to stop or at least control bleeding.

The problem of epistaxis treatment is complicated by the fact that nasal bleeding can occur at any of a variety of locations within the nasal cavity. FIG. 1 illustrates generally the human nasal cavity and indicates the location of the major portions of the nasal cavity, i.e., the anterior nasal cavity, the posterior nasal cavity, and the nasopharynx. In practice, anterior epistaxis generally arises from the septum, the floor of the nose, or the turbinates which are along the outer wall of the anterior nasal cavity. Posterior epistaxis occurs within the posterior nasal cavity typically near its junction with the nasopharynx. The problem with treating epistaxis is further complicated by the limited visibility afforded the physician within the narrow, dark nasal cavity, particularly if bleeding is profuse. Because of these limitations, it is difficult for the physician to determine whether the nasal packing or nasal packing device has been properly positioned, which may result in repeated packing procedures with different devices. Such trial and error techniques are undesirable because of the loss of blood and wasted time. Also, the insertion of nasal packing and packing devices is often painful and uncomfortable for the patient; and when the nasal packing or packing device must be repositioned or reinserted unnecessary pain and discomfort is inflicted on the patient.

A wide variety of nasal packing devices have been developed in an attempt to control nasal bleeding, but unfortunately, none of these devices has met the needs of physicians for ease of use and effectiveness while also providing patients with a less painful treatment. One relatively effective technique for stopping nasal bleeding is with the use of gauze, but this technique typically is relatively slow, as a very large amount of gauze may need to be inserted to control the bleeding, e.g., commonly six feet of gauze. The insertion and removal of the gauze can also be painful and uncomfortable for the patient, with some patients requiring anesthesia or other pain inhibitors.

To address the problems with using gauze, a number of inflatable nasal packing devices have been developed, but again these devices have not met all of the needs of physicians and patients. For example, many devices have been developed and used that provide one or two inflatable members or sleeves. In some devices, one inflatable member is positioned in the anterior nasal cavity and the other is located in the nasopharynx. Each inflatable member is typically formed of elastic material and can be thought of as a balloon. While providing some control over nasal bleeding, devices utilizing balloons typically are ineffective in reaching all areas of the irregularly shaped nasal cavity and typically cause a patient a significant amount of pain during inflation.

More specifically, an elastic balloon does not readily conform to the convoluted surface (turbinates) of the lateral nasal wall or to septal deviations because the wall of a balloon becomes relatively rigid early in the inflation process and becomes progressively stiffer with continued inflation. The initial and continued wall stiffness substantially reduces the effectiveness of a balloon in controlling bleeding from the turbinates and septal concavities. Some of these balloon nasal packing devices have been developed in an attempt to stop posterior epistaxis by compressing the main artery to the interior of the nose (i.e., the sphenopalatine artery) as it enters the nasal cavity and before it forms any branches. However, presently available balloon devices do not address posterior epistaxis caused by branches of the anterior and posterior ethmoid arteries. These devices fail to address the problem that a spherical balloon does not readily conform to the non-spherical anatomy of the nasopharynx and posterior nasal cavity.

Further, the typical balloon or elastic device fails to address problems in controlling epistaxis in patients with deviated septums. The balloon nasal packing devices are relatively effective for treating anterior epistaxis arising from a nasal septal site that is directly compressed by the inflated anterior balloon. However, the effectiveness is limited to the situation in which the septal bleeding site directly matches the generally spherical contours of the inflated balloon. That is, the balloon wall can only compress a bleeding site in the mid-portion of a substantially planar or mildly concave or convex septal deviation as can be seen in FIG. 2. Additional limitations for balloon wall contact exist when the septum exhibits a more remarkable degree of deviation, which is a common finding in the epistaxis patient. A septal deviation is characterized as a convexity, concavity, bone spur, or bone crest as can be seen in FIG. 2. It is at a site of septal deviation that high local airflow turbulence occurs. Mucosal dessication, erosion, and subsequent bleeding are more likely to occur at such a site than in an area of smooth, laminar airflow over a midline planar mucosal surface. Similarly, more posterior nasal sites of high local airflow turbulence are predisposed to epistaxis. FIG. 2 illustrates the lack of contact between the inflated balloon and the concave portion of the septum. Hence, the elastic balloon devices are least effective in areas of the nasal cavity where bleeding is expected to occur in patients with deviated septums.

The use of balloon nasal packing devices has also proven to be very painful to epistaxis patients. Generally, the pain is caused by the high pressure required to inflate the balloon and to force it to fill at least portions of recessed or irregular surfaces within the nasal cavity. As can be understood by anyone who has blown up or inflated a child's balloon, a relatively high pressure is required to initiate the initial stretching of the balloon material. Typically, this initial high pressure must be maintained for at least a period of time to keep the material stretching such that the balloon takes an inflated volume that is pressure dependent, e.g., the balloon wall initially defines a relatively small volume but later defines an inflated volume that depends directly on internal gas pressures and wall material and thickness. The balloons are typically sealed circumferentially to the tube used for inserting and supplying inflating gas to the balloons. With this type of attachment, the balloons typically stretch outward radially from all sides of the tube to initially form an enlarged tube with a circular cross section that increases in diameter at larger distances from the seal locations. Hence, the shape the inflated balloon attempts to form is very different from the irregular nasal cavity of the typical patient shown in FIGS. 1 and 2.

With specific reference to nasal packing devices, the balloon wall exerts the initial high fill pressure outward against any portion of the nasal cavity contacting the balloon exterior, causing the patient pain. The high pressure also typically makes it difficult for the balloon to conform, due to wall rigidity, to irregular shapes and generally to any shape that is not relatively spherical or smooth. With reference to FIG. 2, the relatively rigid balloon wall exerts an especially high pressure point against any projecting septal deformity, which, in turn, causes greater pain for the epistaxis patient. When bleeding occurs at a recess lying under a septal spur or crest, markedly higher inflation pressure is required to stretch the balloon wall toward that recess, thereby, causing the patient even more pain while typically still not providing an adequate contact pressure upon the bleeding site. If contact is not achieved, the pressure must be increased in an attempt to force the balloon into crevices.

Hence, there remains a need for an improved inflatable nasal packing device that addresses balloon-associated high inflation pressure requirements, limitations in reaching recessed bleeding sites, and unacceptably high treatment-induced patient pain levels. Preferably such a device would be easy for a physician to insert, to operate, and to remove while also reducing the amount of discomfort and pain experienced by the patient during and after treatment, e.g., during removal of the device.

SUMMARY OF THE INVENTION

The present invention addresses the above problems by providing an inflatable nasal packing device that utilizes an anterior and a posterior bag for controlling epistaxis in a patient's nasal cavity. The bags are fabricated from relatively inelastic material with surface areas that define interior volumes that are larger than the anterior nasal cavity and than the posterior naval cavity. Each bag can be filled independently with a gas or liquid (such as a saline or the like) at a first lower pressure or fill pressure that allows the oversized bag to (and from the patient's point of view, gently) expand to fill the volume of the anterior and/or posterior nasal cavities, i.e., to obtain good contact surfaces between the bag and the potential bleeding sites. To improve expansion at the lower fill pressure, the outer surfaces of the bags are lubricated to reduce friction between the bag and the nasal wall and between contacting surfaces of the bag itself. Once positioned in abutting contact with the nasal tissues, each bag can be pressurized by the addition of more gas or liquid to a second higher or bleeding control pressure that is then applied by the bag to the adjacent nasal wall for a period of time to stop epistaxis. Epistaxis treatment with the device is further enhanced by design of the anterior bag to extend posteriorly, so as to overlap the uninflated posterior bag's potential of coverage. Reciprocally, the posterior bag design allows anterior expansion to overlap the anterior bag's potential coverage area. Thus, when both bags are inflated, each conforms to the other; this feature allows a bleeding site at the junction of the two bags to be effectively compressed as if a single bag was present at such a site.

More particularly, this invention provides an inflatable nasal packing device having a flexible tube that can be removably inserted into the nose and that has a length, e.g., up to 7 centimeters or more (shorter for pediatric embodiments), that enables it when inserted to extend from the nasal vestibule into the nasopharynx. A first inflatable bag surrounds and is attached to the anterior portion of the tube. A second inflatable bag surrounds and is attached to the posterior portion of the tube. Each bag wall is soft, compliant and minimally distensible and is sealed with an elongate seal along the length of the distal side of the tube (as well as circumferential seals at each end of the bag). Each bag wall surface area is substantially fixed because the wall material is non-elastic, and the surface area is selected to define a relatively pressure independent inflated volume that is significantly greater than the relevant nasal volume. The bag characteristics of having a large fixed surface area of flexible yet non-elastic material allow low pressure filling of the bags and gentle conforming or reshaping to the relevant nasal anatomy by snake-like or amoeboid pseudopod-like movement prior to the exertion of higher bag pressure which is adequate to control bleeding.

According to a method of using the device for controlling epistaxis, the tube and bags of the device are initially inserted into the nasal cavity with the bags deflated. Either or both of the bags are then inflated concurrently or sequentially with air or fluid at a low fill pressure. Once in place, pressure is increased until sufficient pressure to control the bleeding site is attained, i.e., a second or bleeding control pressure. The first bag fills the anterior nasal cavity, and the second bag fills the posterior nasal cavity and nasopharynx. In one embodiment, a length of overlap is provided by sealing the bags in an adjacent manner along the length of the tube, which disallows a gap in coverage between the anterior and posterior bags.

In one embodiment, the tube has three lumens. One for providing an air passageway from outside the patient's nasal cavity to the nasopharynx, and one each for independently filling the bags. The bags are typically inflated and deflated with a valved catheter with a reservoir compartment fluidically connected with tubes to the two fill lumens of the tube. Upon bag deflation, the device is then removed from the nose and nasal cavity.

One objective of the present invention is to provide an inflatable nasal packing device that is effective in treating both anterior epistaxis (bleeding) and posterior epistaxis in a manner that obviates the rigidity and high pain levels dictated by the inflation principles of a balloon. The present invention can be thought of as reversing the principles of inflation inherent with a balloon. Specifically, a balloon is quickly a high-pressure system (at the beginning of inflation) and, second, is expected to expand toward the bleeding site as the balloon wall continuously loses elasticity with further inflation. A balloon initially defines a small volume and then when inflated defines a larger volume, i.e., has a variable surface area and enclosed volume which are pressure dependent. A balloon begins as an under-volume (i.e., smaller volume than the nasal cavity to be filled), high pressure system which then attempts to reach a bleeding site, while simultaneously becoming increasingly rigid and less able to conform to nasal cavity contours during the process of inflation.

In contrast, the device of the present invention reaches the bleeding site during low pressure filling and prior to exertion of relatively high pressure. The device begins as a collapsed oversized bag that initially fills the nasal cavity and conforms to nasal cavity contours as a low-pressure system. Relatively high pressure is not exerted until the anatomic boundaries of the relevant nasal cavity have been matched. The device of the invention allows relatively low pressure advance over the nasal cavity contours with a marked decrease in inflation-related pain for the patient, as well as increasing the likelihood of applying direct pressure to the bleeding site.

The advantages of the design of the inflatable nasal packing device include: (1) minimization of pain for the patient during device inflation; (2) marked enhancement of the physician's ability to perceive inflation pressure being exerted against nasal cavity tissue (e.g., elimination of significant resistance to inflation that is inherent in a balloon wall and that makes it difficult for a physician to perceive inflation pressure when using or squeezing small "tell tale" bags (not shown) adjacent to the inflation valve); (3) significantly increased likelihood of reaching the bleeding site; (4) elimination of a gap between the anterior and posterior compartments, as occurs between two balloons; (5) avoidance of especially high pressure points at spurs, convexities, and recesses within the nasal cavity; (6) decreased pain medication requirements for the patient related to pack insertion and maintenance; (7) enhanced ease of pack insertion and removal, which is further enhanced by lubrication of the bags that reduces adherence of blood clots and re-bleeds; (8) self-seating pack design characteristics not relying on advanced skill and experience level of physician; (9) virtual assurance of emergency department physician's ability to quickly control anterior and posterior epistaxis that obviates repeated packing attempts and/or inherent time delay associated with ear, nose, and throat specialist referrals; and (10) reduction of hospitalizations and epistaxis patient mortality.

DETAILED DESCRIPTION OF THE PREFERRED EMBODIMENTS

The present invention is directed to an inflatable nasal packing device that includes two bags that are oversized relative to the anterior and posterior nasal cavities, are formed of flexible but relatively inelastic material, and can be independently or concurrently filled and pressurized. The use of bags selected to have interior volumes (when inflated in an unrestrained state) larger than the irregular space within which they are expanded and nasal wall surfaces to which they are expected to comply and match contour allows the device of the present invention to function in substantially the reverse fashion of a common elastic nasal packing device. Specifically, the bags of the present invention are filled gently with a gas or other fluid at a first lower fill pressure. Once positioned in contact with substantially all or most of the intranasal surfaces, the bags are inflated further or pressurized to a second higher pressure (e.g., a "bleeding control pressure"). In contrast, common elastic devices or balloon-based devices are filled initially at relatively high pressure, which is required to overcome the resistance to stretching of the balloon walls but which simultaneously causes increasing balloon wall rigidity. This increasing rigidity results in greater difficulty for the balloon wall to conform to irregular shapes (such as those formed by nasal ridges), causing excessive pain levels for the epistaxis patient.

Figure 9:
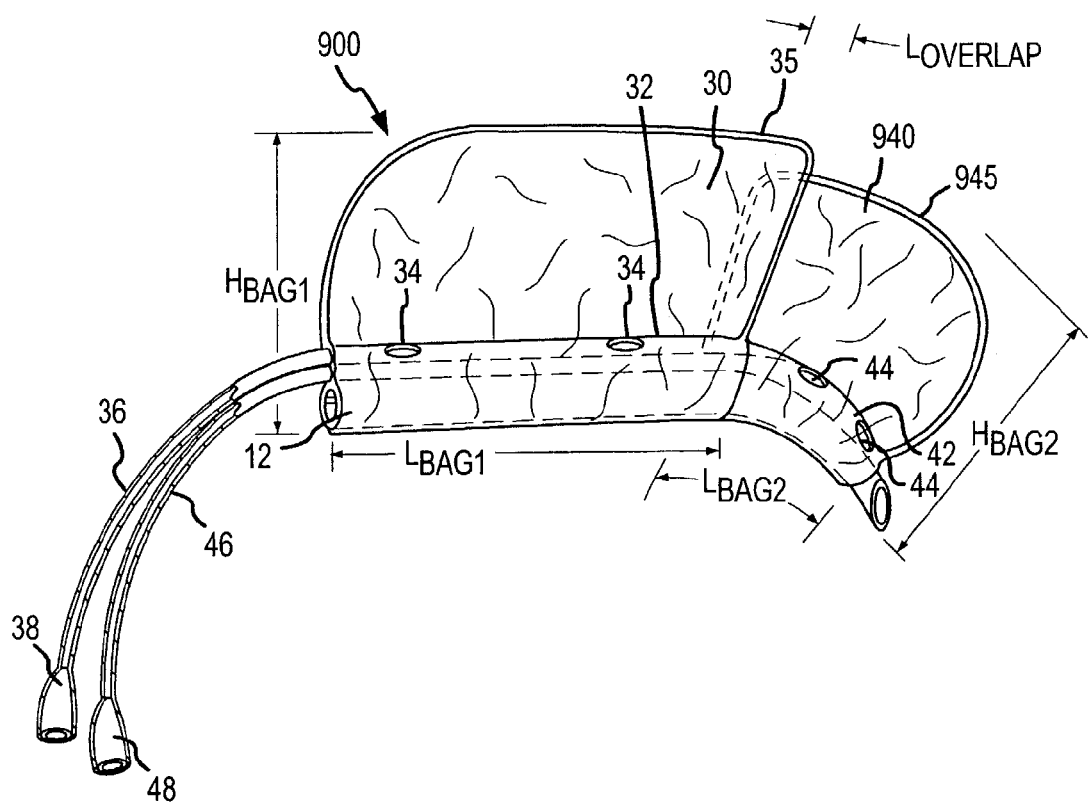
FIG. 9 is a side view similar to FIG. 3 illustrating another embodiment of an inflatable nasal pack device according to the invention that includes two oversized bags but positioned along the structural tube to overlap or be adjacent along an overlap length measured along the longitudinal axis to the tube.
Figure 10:
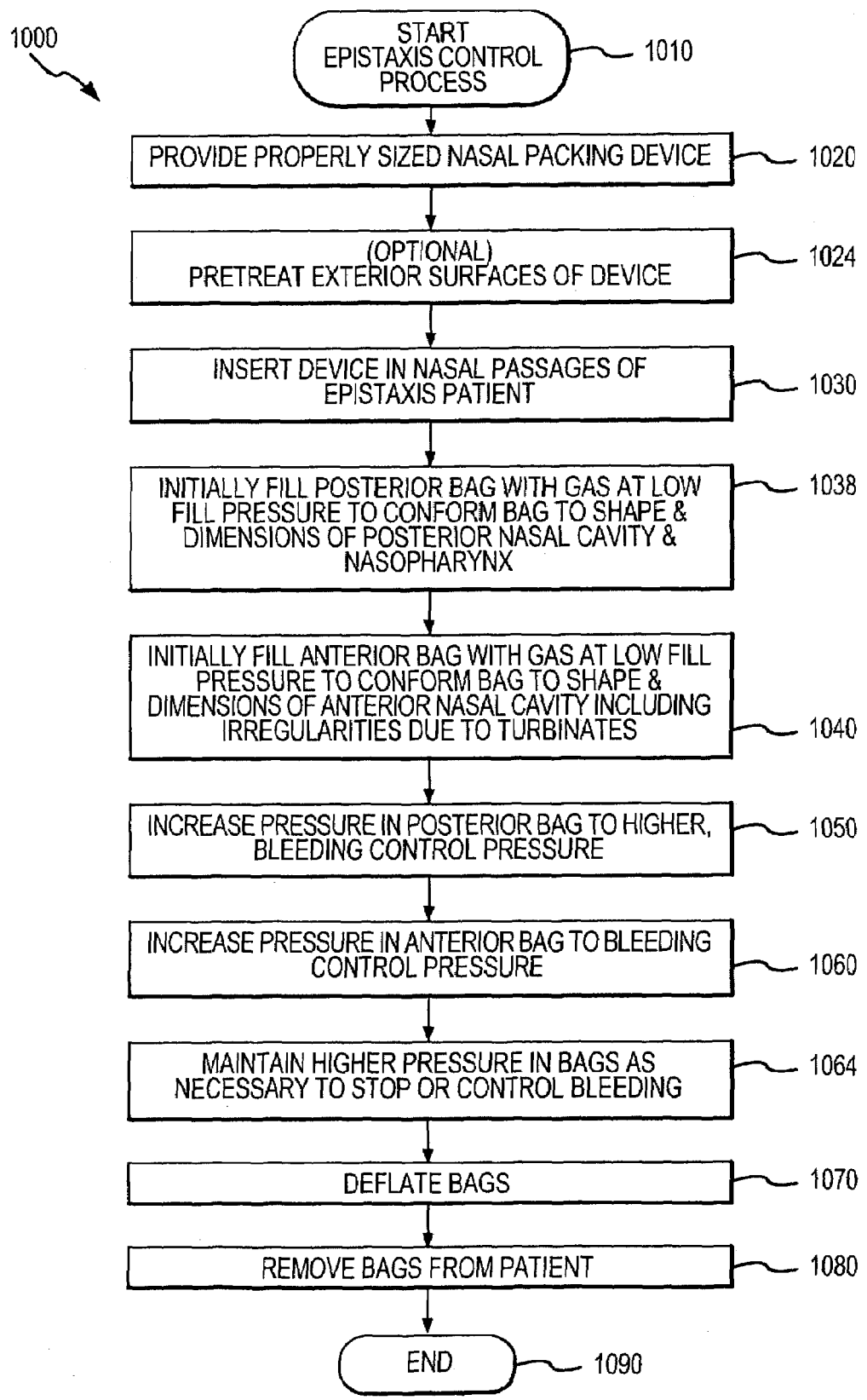
FIG. 10 illustrates exemplary steps of an epistaxis control process of the present invention.

The following description begins with a general overview of how the features of the invention provide useful solutions to the problems with previous nasal packing devices. Then, with reference to FIGS. 3–8, one useful embodiment of an inflatable nasal packing device is described illustrating the use of two oversized and independently operable bags of inelastic material to control epistaxis. FIGS. 3–8 illustrate the device inflated prior to insertion to show unrestrained or potential dimensions of the device (e.g., the relatively fixed surface area of the bags which defines the oversized volume of the bags), illustrate the irregular spaces that need to be reached within a human nasal cavity to control bleeding, illustrate initial insertion of an uninflated device, and also illustrate use of a device within a patient (e.g., initial low pressure fill and later high pressure inflation). With reference to FIG. 9, another embodiment of the invention is described in which a somewhat smaller anterior bag is used that is positioned along the insertion and fill tube to provide a length of coverage or application overlap between the two bags to provide better control over epistaxis at the juncture of the two filled and inflated bags. Finally, FIG. 10 is provided to facilitate and support discussion of a method of using inflatable nasal packing devices, including the use of pretreatments such as lubrication of external bag surfaces to overcome bag-to-bag and bag-to-tissue friction, surface tension, or other resistance in properly positioning and inflating the two bags within the nasal cavity.

Generally, to provide epistaxis control advantages, the present device includes a flexible tube, such as a two or three-lumen tube, that can be inserted into the nasal cavity and that has a device length that enables the tube or part of the tube to extend from the anterior septum to the nasopharynx. Two inflatable bags are positioned along the tube to surround tube and are sealed circumferentially at the bag ends. As a result, when the device is inserted in a nasal cavity, one bag is positioned adjacent the anterior nasal cavity and one bag is positioned adjacent the posterior and nasopharyngeal portions of the nasal cavity. During operation, the first bag fills the anterior nasal cavity and the second bag fills the posterior nasal cavity and nasopharynx when filled and then pressurized or inflated at a higher pressure. Important bag wall physical characteristics include: (1) it is soft; (2) it is quite compliant; (3) it is minimally distensible or non-elastic; and (4) its surface area is oversized relative to the corresponding nasal cavity volume to define a volume larger than the respective nasal cavity section.

These characteristics can be readily contrasted with the inherent balloon wall or elastic member characteristics that include: (1) its surface prior to inflation is markedly undersized relative to the corresponding nasal cavity volume (i.e., the surface area of the balloon is variable and dependent on pressure of contained gases); (2) stretching of the relatively distensible wall is required for inflation; (3) the elastic wall significantly resists stretching (inflation); (4) the wall rigidity increases with continued inflation; and (5) the balloon tends to assume a predetermined shape, as determined by its manufacturing specifications and the way in which it is sealed to the insertion tube. The combination of these characteristics causes a balloon used as a sealing device to become a relatively high-pressure system at the onset of the inflation process, which increases the rigidity of the balloon wall. The relatively rigid balloon wall is then forced by the same or higher gas pressures to attempt to conform to irregular nasal contours despite the ever increasing stiffness of the balloon wall associated with continued inflation. In practice, the balloon or elastic member wall generally cannot be forced to mate with all of the nasal wall surfaces and the high-pressure inflation process inflicts pain to the patient.

In contrast, the device of the present invention uses two inflatable, oversized bags that are initially and remain a relatively low-pressure system as the bags fill and conform to contours within the nasal cavity. The bag walls remain compliant and flexible because they are oversized with a set surface area. Relatively high pressure is not applied until the nasal cavities are filled by the bags. Compression of the bleeding sites is then performed with exertion of even, higher pressure by the external surfaces of the bags throughout the relevant nasal cavity area, which minimizes overall intranasal pressure against tissues and prevents high pressure points that cause a patient discomfort.

Figure 4:
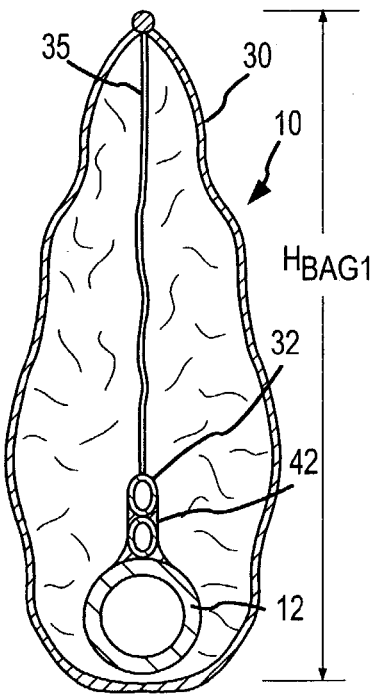
FIG. 4 is a cross sectional view of the device of FIG. 3 taken at line 4—4 better illustrating the location of the bottom elongate seal used to seal the bags to the structural or insertion tube of the nasal packing device of the invention.

Further, during the inflation process the oversized, compliant bags of the present device follow contours, ridges, and recesses of the nasal cavity. Inflation occurs at a relatively low pressure that causes the bag to advance in amoeboid, pseudopod-like movement. Each bag surrounds the tube and is sealed at its ends to the insertion tube with a small volume of the bags provided along the underside of the tube (as shown in FIG. 4). This underside bag component exists sos that its expansion will address any bleeding site along the floor of the nasal cavity. The ends of the anterior bag are sealed at a first and second location along the insertion tube: whereas the ends of the posterior bag are sealed at a third and fourth location along the insertion tube. This sealing technique allows each bag to conform to anterior/posterior septal lateral nasal wall, nasal floor, and nasal roof bleeding sites. Prior to insertion, the bags' exterior and/or interior surfaces may be pretreated such as with the application of hemostatic agents, antibacterial agents, or antiviral agents. Additionally, pretreatment of these bags with ionization or other surface treatment will lessen the tendency of blood clots to adhere to the device. Thus, the potential for rebleeding secondary to clot adherence to the device will be decreased. A lubricant, such as K-Y™ Jelly or other lubricant common in the medical industry suitable for contact with human nasal cavity, is applied to the exterior surfaces of the bag to enable the bag to more readily be filled and conform to the nasal cavity. The insertion tube includes a lumen for allowing passage of air or therapeutic oxygen through the device and nasal cavity even when the device is fully inflated. Those skilled in the art will, once these improvements and features are understood, determine additional features that can be readily added to the device. For example, the device may be further modified by the insertion of a keel or other device within the bag(s) to assist in bag inflation for accommodating severe nasal anatomic obstruction situations and/or with bivalving the bag(s) in order to pass around an unusually prominent septal spur.

Generally, to provide epistaxis control advantages, the present device includes a flexible tube, such as a two or three-lumen tube, that can be inserted into the nasal cavity and that has a device length that enables the tube or part of the tube to extend from the anterior septum to the nasopharynx. Two inflatable bags are positioned along the tube to surround the tube and are sealed circumferentially at the bag ends. As a result, when the device is inserted in a nasal cavity, one bag is positioned within the anterior nasal cavity and one bag is positioned within the posterior and nasopharyngeal portions of the nasal cavity. During, the first bag fills the anterior nasal cavity and the second bag fills the posterior nasal cavity and nasopharynx when filled and then pressurized or inflated at a higher pressure. Important bag wall physical characteristics include: (1) it is soft; (2) it is quite compliant; (3) it is minimally distensible or non-elastic; and (4) its surface area is oversized relative to the corresponding nasal cavity volume to define a volume larger than the respective nasal cavity section.

Figure 1:
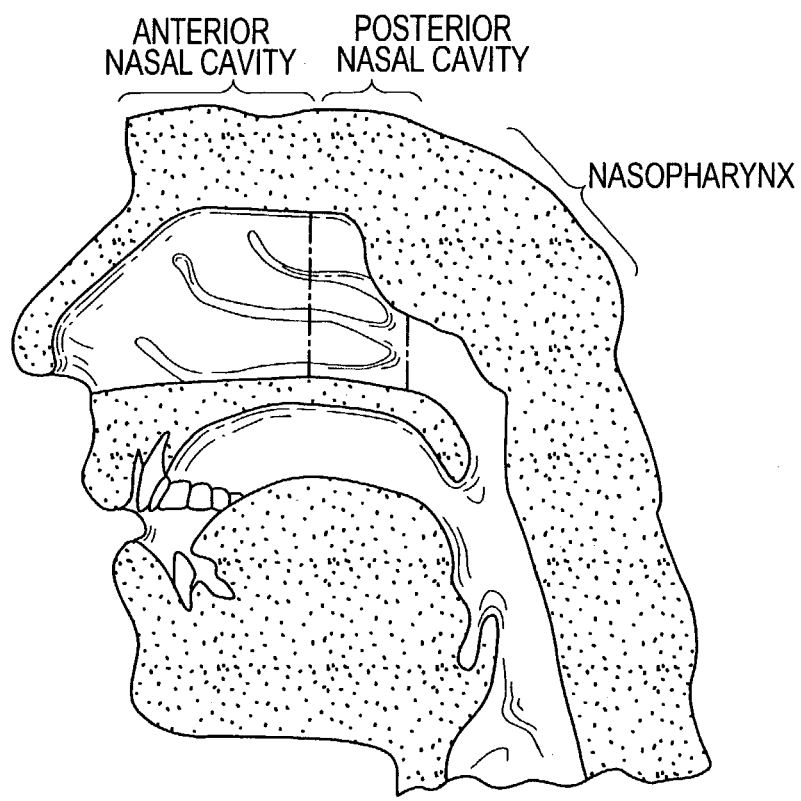
FIG. 1 is a partial, side sectional view of a human head illustrating the parts of the nasal cavity.
Figure 2:
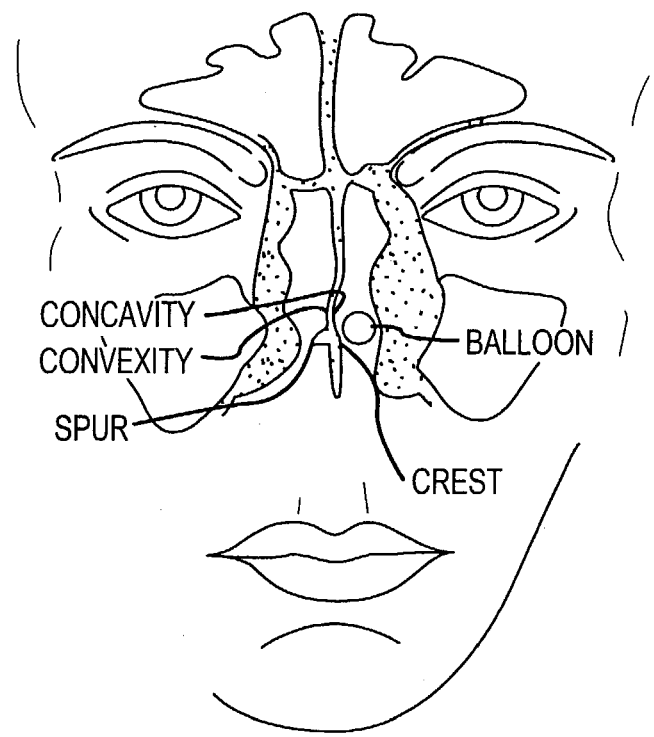
FIG. 2 is a partial, front sectional view of a human head illustrating portions of a nasal cavity with a deviated septum illustrating difficulties in using a balloon or elastic device for controlling epistaxis.
Figure 3:
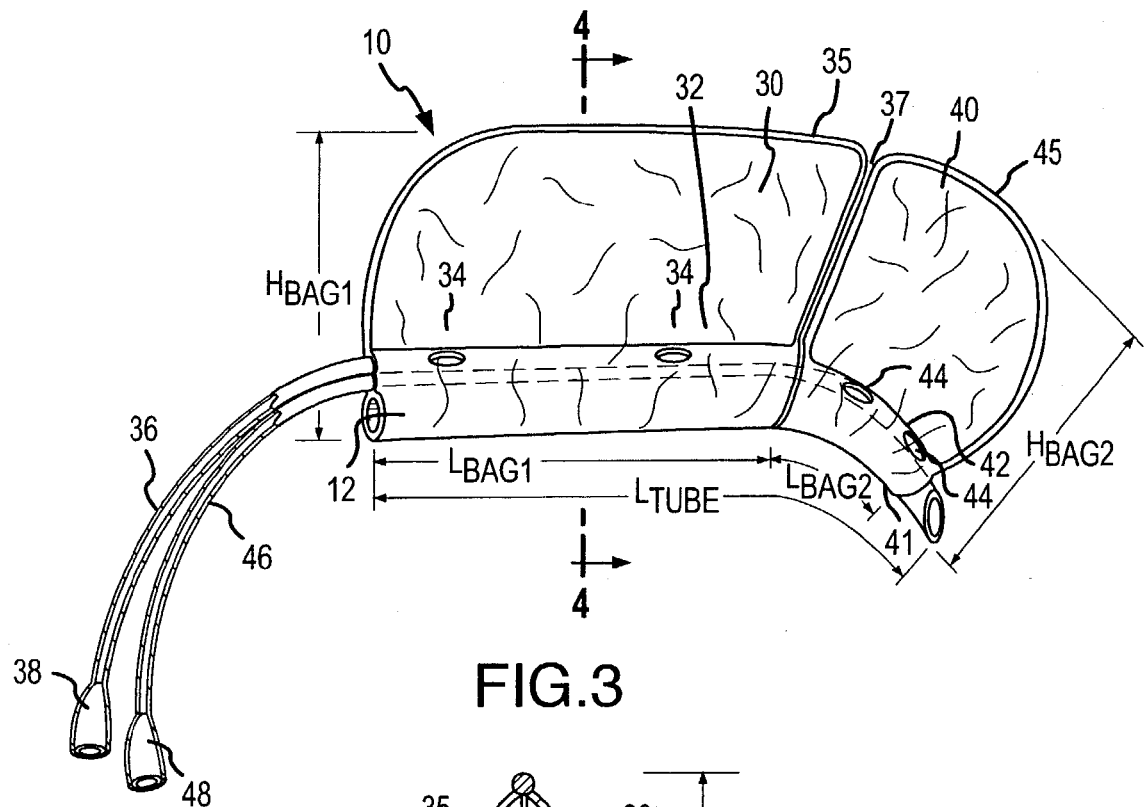
FIG. 3 is a side view of an inflatable nasal packing device according to the present invention illustrating a first and a second bag in an inflated, unrestrained state to illustrate fixed (or potential) surface area of the bags and component dimensions.

The tube 12 is preferably made of a pliable, flexible material, such as PVC, polyurethane, or another non-toxic material compatible with the nasal lining tissue, with PVC being used in one embodiment to offer sufficient support or stiffness to push the device 10 into the nasal cavity to the posterior region. The tube 12 may optionally have a hollow longitudinal section as shown in FIGS. 3 and 4 that provides an air passageway through the device 10. Such a passageway is provided even when the bags 30, 40 are inflated during insertion into a nasal cavity. The tube 12 may be straight or may be manufactured to be slightly curved to aid in the insertion and removal of the device from a nasal cavity.

Figure 5:
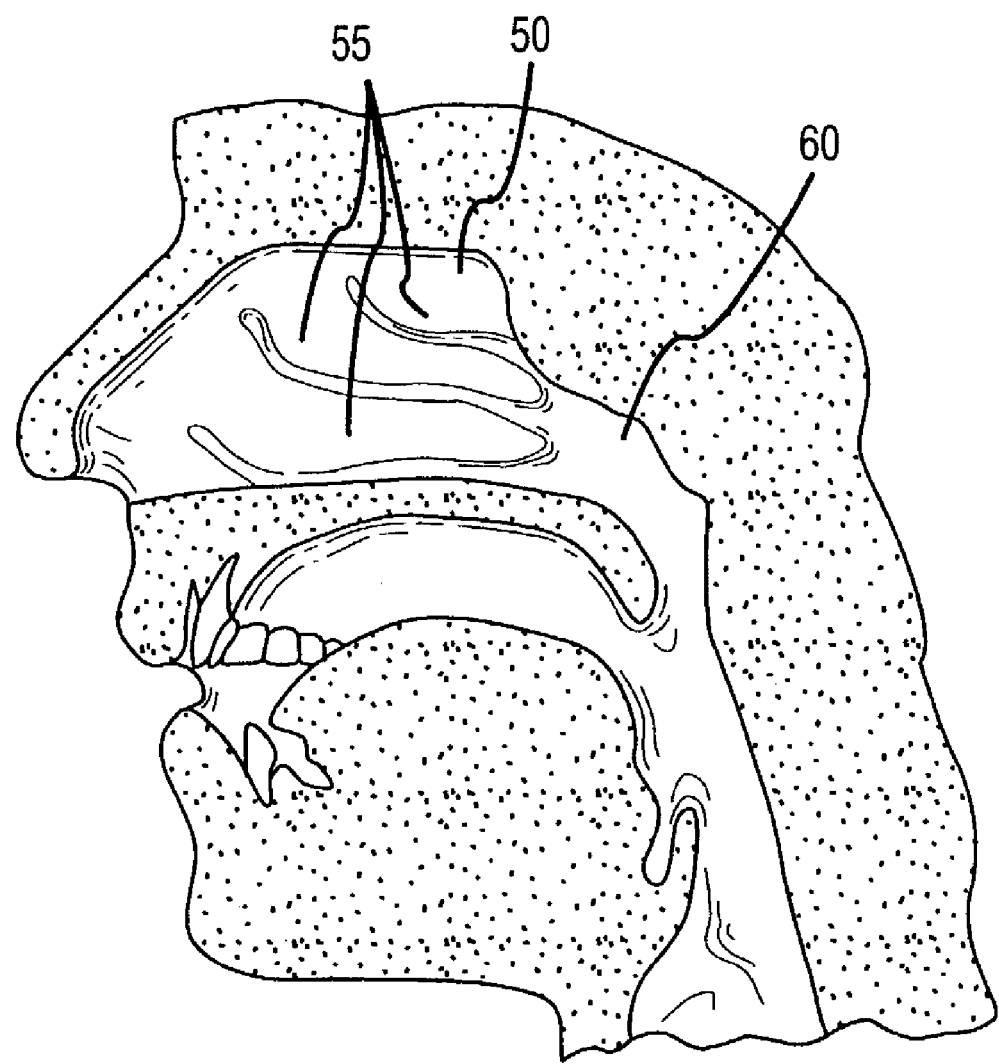
FIG. 5 is a side section view similar to FIG. 1 of a human head and the nasal cavity further illustrating turbinates that create an irregular pattern or contours in the nasal cavity making sealing of the nasal wall more difficult.
Figure 6:
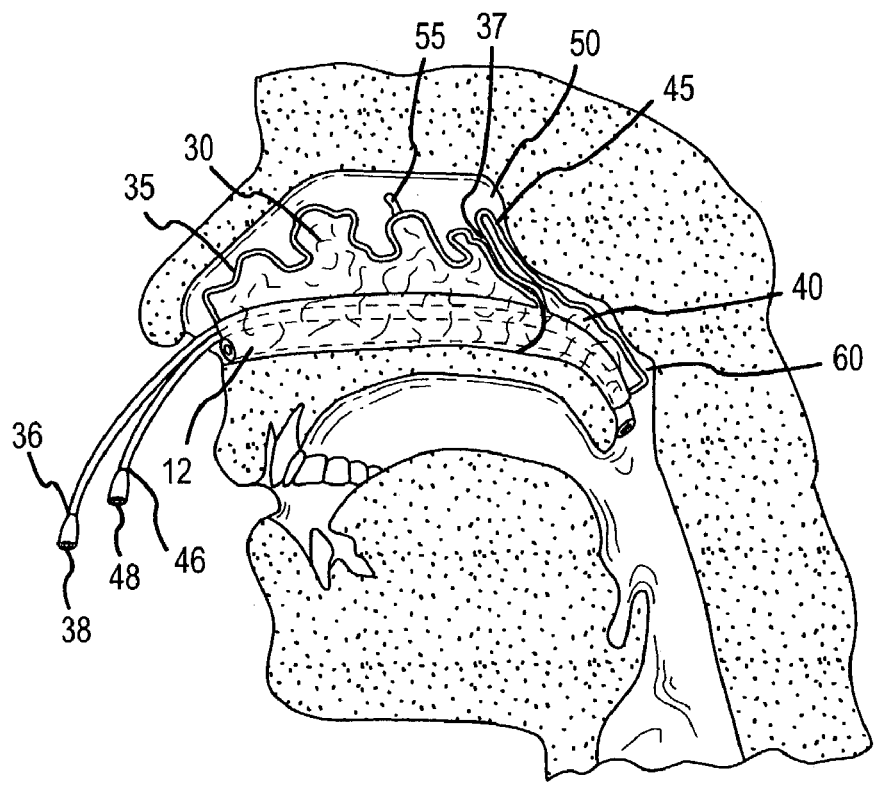
FIG. 6 illustrates the device of FIG. 3 inserted within a patient's nasal cavity and being initially filled at a low fill pressure which shows the irregular or amoeboid pseudopod-like movement or expansion of the bags to fill the nasal cavity volume.

FIG. 5 shows a cross-sectional view of the nasal cavity 50 prior to insertion of the device 10. The device 10 is designed to be easily inserted through the patient's nostril with the bags 30, 40 deflated, as shown in FIG. 6. The length of the tube, $L_{TUBE}$, is selected so that the posterior portion of the tube extends into the nasopharynx 60 when the anterior portion of the tube is positioned within the nasal cavity 50. FIG. 5 is useful for showing the irregularities in the size and shape of the nasal cavity 50. The sidewalls of the nasal cavity 50 are lined by a series of ridges 55 of bone, commonly known as turbinates, that are covered with soft tissue. The turbinates 55 combine to create an irregular, convoluted surface to which a balloon cannot conform but which, as discussed below, the bags 30, 40 of the present invention can gently comply during filling and then mate with more firmly during application of higher pressures.

As shown in FIGS. 3–8, a first inflatable bag 30 is attached to the anterior portion of the tube 12 or to the portion of the tube 12 which will be positioned in the anterior portion of the nasal cavity 50. Similarly, a second inflatable bag 40 is attached to the posterior portion of the tube 12 or to the portion of the tube which will be positioned in the posterior and/or nasopharynx portion 60 of the nasal cavity 50 during use of the device 10. The bags are made of a thin, flexible plastic film, such as urethane or polyvinyl chloride (PVC). The first bag 30 is oversized in relationship to the volume of the anterior nasal cavity 50, while the second bag 40 is oversized in relationship to the volume of the posterior nasal cavity and nasopharynx 60. The bags 30, 40 are positioned serially and adjacent on the tube 12 to either abut when filled and inflated to a higher pressure, as shown at 37, or to provide a slight gap.

The oversized feature of the bags 30, 40 is significant to the invention and is provided by using materials for the bag walls that is flexible but yet relatively non-elastic. The flexibility allows the bag 30, 40 to be reduced in size when empty while the non-elasticity allows the potential or maximum inflated volume of the bag to be relatively fixed. In other words, the fixed surface areas of the bags 30, 40 defines the potential volume to be held by the bags 30, 40 and such volume is relatively pressure independent. This allows the bags 30, 40 to be filled slowly at low pressure and then further pressurized without an increase in bag volume to stop or control bleeding. A number of materials may be used for the bags 30, 40 to provide such flexibility and strength while being non-elastic. For example, PVC, polyurethane, and similar materials may be utilized for the walls of the bags 30, 40. In one embodiment, polyurethane is provided in a thin sheet (e.g., about 0.001-inch thick) for use in forming the bags 30, 40. Testing showed that this material provided adequate strength for applying a force 2.5 times greater than the force needed to stop bleeding, was flexible enough to comply into nasal contours (especially when treated with a lubricant) without noticeable stretching, and was relatively useful in limiting blood clot adherence (especially when treated by ionization).

Another important feature defining the filled and inflated shape of the bags 30, 40 is the method used in sealing the bags 30, 40 to contain pressurized gas. As shown in FIGS. 3 and 4, the bags 30, 40 are sealed circumferentially at the ends to the tube 12 (and to catheters 32, 42), such as with instant adhesive, a hot-melt adhesive, and/or radio frequency (RF) welding and with edge seals 35, 45 that create a bag from two flat sheets (e.g., such as by heating the edges of the bags 30, 40 or by utilizing an RF sealing method). The positioning of the bags 30, 40 relative to the tube 12 and subsequent sealing is selected carefully to provide the desired inflated shape for the bags 30, 40 to better control epistaxis. Specially, with reference to FIG. 8, it is desirable for the bags 30, 40 to inflate almost entirely in one direction upward away from the tube 12. This allows the base of the tube and small volume portions of the bags 30, 40 shown in FIG. 4 to be positioned along the relatively planar base of the nasal cavity 50 and nasopharynx 60 where bleeding is not typically a problem. The larger volume portions of the bags 30, 40 extend away (or upward) from the tube 12 into the cavities 50, 60 in which bleeding is occurring. To obtain this desired shaping of the bags 30, 40, the bags 30, 40 enclose the tube 12, as shown in FIGS. 3 and 4, and are sealed at the ends of the bags 30, 40 to be airtight.

During use, the device 10 is normally inserted into the nasal cavity 50 with the bags 30, 40 in a deflated state to minimize patient discomfort as shown in FIG. 6. An antibiotic ointment may be applied as a pretreatment and/or a water-based gel or other lubricant can be used to coat the exterior surfaces of the bags 30, 40 for lubrication to reduce resistance to filling and compliance with nasal wall contours. Following insertion of the device 10, the bags 30, 40 can be independently or concurrently filled to position and shape the bags 30, 40 and then inflated by supplying low and then higher pressure air or fluid from an external source (not shown), through corresponding tubes 36, 46 that lead to catheters 32, 42 (or lumens) extending along the tube 12. This is shown most clearly in FIGS. 7 and 8. The air or fluid flows through a series of fenestrations or openings 34 in the first catheter 32 to inflate the first bag 30. Similarly, the second bag 40 is inflated by supplying air or fluid through fenestrations 44 in the second catheter 42. Any number of openings 34, 44 may be used that are selected to fill and inflate the bags 30, 40, and in one embodiment, two spaced-apart openings 34, 44 are provided (as illustrated) in the lumens or catheters 36, 46 to provide an inlet/outlet for gas or other fluid to enter and exit the bags 30, 40 via catheters 36, 46. Control valves 38, 48 can be provided to control escape of the air or fluid after the bags 30, 40 have been inflated, e.g., one-way valves can be provided at the end of the tubes 36, 46 to prevent gas from flowing out of the bags 30, 40.

Figure 7:
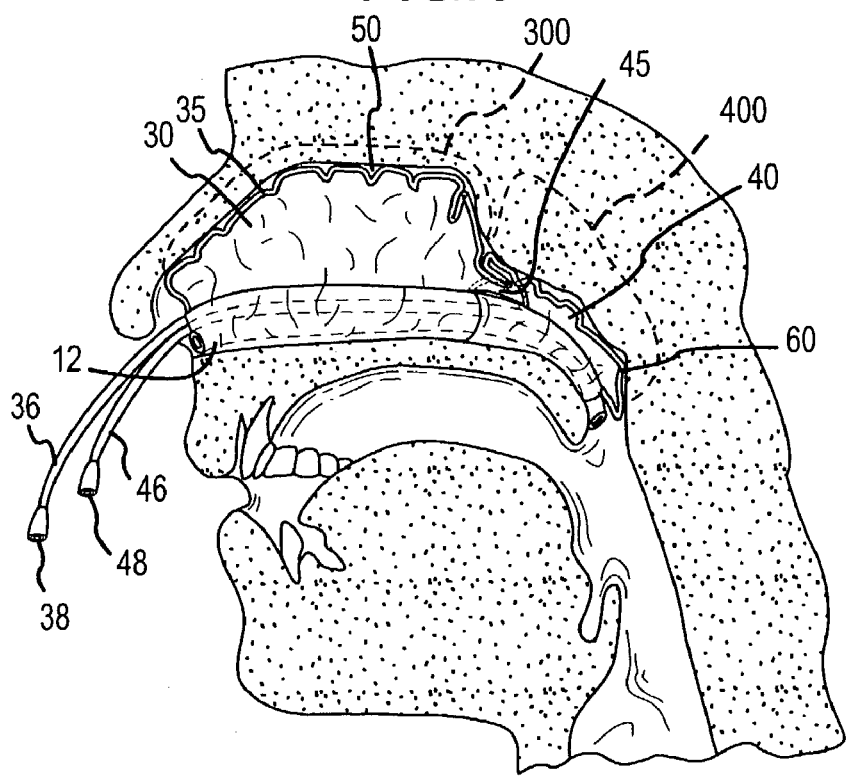
FIG. 7 illustrates the nasal cavity with the device inserted of FIG. 6 at a point of near completion or completion of filling and/or during the application of a higher second pressure or bleeding control pressure to apply a desired pressure to the nasal tissues, i.e., to the bleeding sites of the nasal cavity and further illustrating by superposition the bags as they would appear if allowed to fully inflate to stress the fact that the bags have a fixed surface area that defines volumes greater than the nasal cavities.
Figure 8:
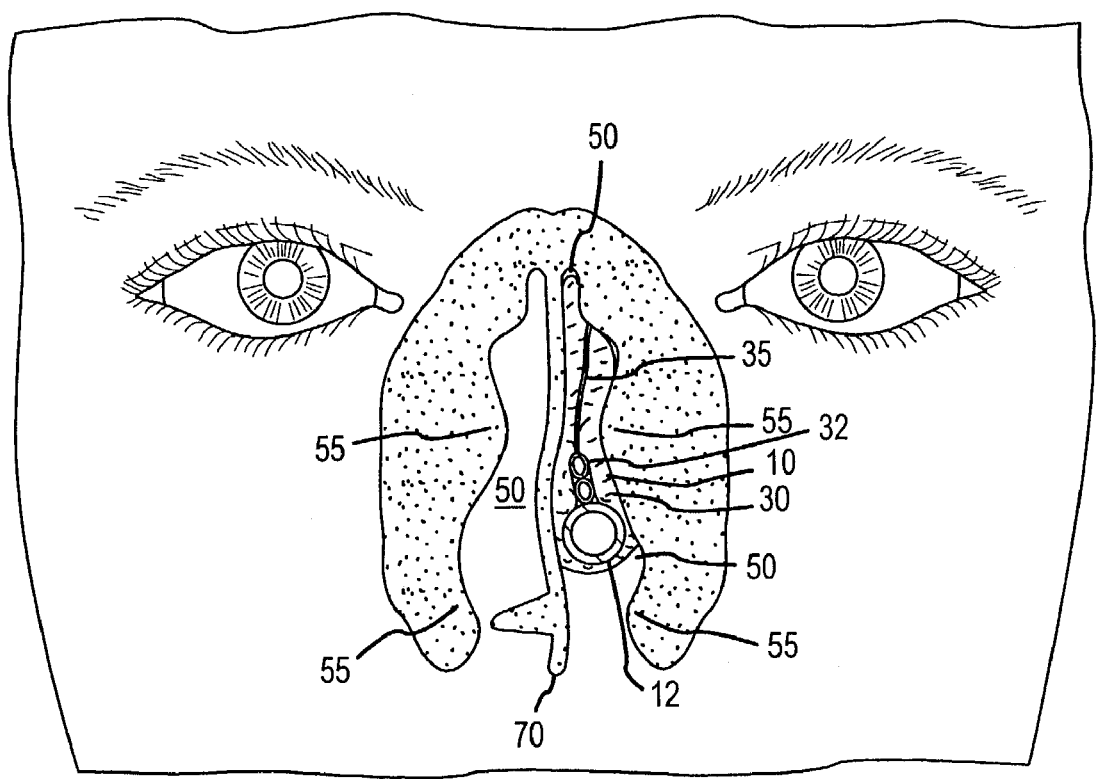
FIG. 8. is a partial sectional view of the nasal cavity with the inserted and inflated device of FIG. 7 showing the irregular expansion of the bag into concavities or recessed areas of the nasal cavity created by turbinates.

After insertion as shown in FIGS. 6, 7, and 8, when the first bag 30 is inflated, it substantially blocks the nasal cavity 50 without a significant degree of bag wall stretching or distention due to the relatively oversized dimensions of the bag 30 and use of a relatively inelastic material. This allows the bag 30 to conform to irregularities in the size and shape of the nasal cavity 50. The sidewalls of the nasal cavity 50 are lined by a series of ridges 55 of bone covered with soft tissue, commonly known as the turbinates, shown in FIGS. 5 and 8. The turbinates 55 create irregular, convoluted surfaces to which a balloon cannot conform. In contrast, the flexible, oversized bag 30 in the present invention is much better at adapting to such irregular surfaces than a balloon. This makes the present invention especially well suited for treating patients 30 who have septal deviation, suffered trauma, or undergone surgery involving the nasal cavity. When inflated, the bag 30 applies evenly distributed pressure on the interior surfaces of the nasal cavity 50 to terminate nasal hemorrhage. The second bag 40 is designed in a similar manner with dimensions sufficiently large to substantially block the posterior nasal cavity and nasopharyrx 60 without stretching or distending the bag wall, as shown in FIGS. 7 and 8. Here again, the second bag 40 is sufficiently oversized and flexible to conform to irregularities in the interior surfaces of the nasopharynx 60, and its use provides a relatively uniform application of pressure on the interior surfaces of the nasopharynx 60 to terminate nasal hemorrhage.

Each bag 30 or 40 can be independently deflated following treatment by opening their respective control valves 38 and 48. The device 10 can be removed from the nasal cavity through the patient's nostril by pulling on the tube 12 or the tubes 36, 46. In the preferred embodiment of the present invention, the first bag 30 completely surrounds the anterior portion of the tube 12 to separate the tube 12 from the septum 70 when the bag 30 is inflated. As shown in FIG. 8, this allows the bag 30 to conform to the contours of the septum 70 and results in a more uniform application of pressure. The second bag 40 can also be designed to completely surround the posterior portion of the tube 12 to provide a more uniform pressure distribution within the posterior nasal cavity and nasopharynx 60.

The size and shape of the two bags 30, 40 can be varied to successfully practice the invention, and may be varied to provide good epistaxis control in average adults and in average children (e.g., larger nasal cavities and smaller nasal cavities). Preferably, however, the first bag 30 is provided with an adequate fixed surface area in the wall material to define a volume that is anterior nasal cavity while the second bag 40 is similarly configured to be oversized in volume relative to the posterior nasal cavity. Using CT scans of adult nasal cavities, the inventor determined that the range in unilateral nasal volume for an epistaxis patient is between about 16 cubic centimeters (cc) to about 34 cc for the anterior nasal cavity 50, with an average volume of about 24 cc. There was less variability in the volume of the posterior cavity 60 which averaged about 10 cc. Hence, with the desired shape of the bags 30, 40 being provided by the positioning of the end seals relative to the bags 30, 40 and the positioning of the bags 30, 40 over the tube. The other dimensions of the bags 30, 40 can be selected to provide the fixed surface area to obtain volumes greater than the above determined volumes for the two nasal cavities 50, 60. These dimensions are shown well on FIGS. 3 and 4. In one embodiment, the following dimensions were utilized for bag 30: a bag height, $H_{BAG\ 1}$, of about 2 to 3 inches and more preferably about 2.5 inches and a bag length, $L_{BAG\ 1}$, of about 3 to 4 inches and more preferably about 3.5 inches. The dimensions of bag 40 were: a bag height, $H_{BAG\ 2}$, of about 1 to 2 inches and more preferably about 1.5 inches and a bag length, $L_{BAG\ 2}$, of about 1 to 3 inches and more preferably 2 inches. Of course, smaller dimensions are appropriate for smaller nasal cavity volumes, such as in children, with the important consideration being use of surface areas for the bags 30, 40 that result in an interior volume being defined that is greater than the corresponding nasal cavity 50, 60. Such oversizing is shown in FIG. 7 relative to the nasal cavities 50, 60. Lines 300, 400 illustrate the potential volumes of bags 30, 40 which would be reached if the bags 30, 40 were not restrained by the contact achieved with the nasal walls (for example, see FIGS. 3 and 4 that illustrate the bags 30, 40 in filled and unrestrained state).

In some cases, the control of epistaxis is enhanced by having the two bags overlap in their area of coverage within the nasal cavity rather than merely abutting. In FIG. 9, an embodiment of an inflatable nasal packing device 900 is illustrated that is configured to achieve such overlapped coverage, specifically in the regions of the nasal cavity in or between the anterior and the posterior cavities. As discussed previously the ends of the anterior bag are sealed at a first and second location along the insertion tube; whereas the ends of the posterior bag are sealed at a third and fourth location along the insertion tube. In this particular embodiment, the end of the anterior bag 30 located most distal to the one way valves 38 and 48 is sealed at the first location and the end most proximal to the one way valves 38 and 48 is sealed to the insertion tube at the second location. Furthermore, the end of the posterior bag 940 located most proximal to the one way valves 38 and 48 is sealed to the insertion tube at the third location while the end located most distal to the one way valves is sealed at the fourth location. As shown, the second or posterior bag 940 with a seal 945 is shown to be positioned adjacent to the first or anterior bag 30 by sealing the bag 940 at its end "upstreamt" from the end of the bag 30. As measured along the longitudinal axis of the tube 12, this provides a length of overlap coverage, $L_{OVERLAP}$, for the two bags 30, 940 such that when the bags are filled, the overlap portions of the bags 30, 940 better fill the contours of the nasal cavities 50, 60. The size of such overlap may vary but typically, the overlap length, $L_{OVERLAP}$, is selected from the range of 0.25 to 1 inch and in one embodiment, is about 0.7 inches. The overlap may be achieved by increasing one or both of the bag lengths, $L_{BAG1}$, $L_{BAG2}$. Also, in this illustrated embodiment, the bags 30, 940 are also shown to be more clearly sized for the posterior and anterior nasal cavities with the first bag 30 having a larger bag height, $H_{BAG1}$, than the height, $H_{BAG2}$, of the second bag 940.

FIG. 10 illustrates exemplary steps in using the embodiments of the inflatable nasal packing devices 10, 900 in an epistaxis control process 1000. The process 1000 begins at 1010 typically with selecting the proper dimensions for the device to be inserted in a patient, with an important aspect being that the length of the tube 12 is adequate to pass to or through the nasopharynx and that the bags have adequate lengths and heights to have a surface area that defines a larger volume than the portions of the nasal cavity being filled by the bags. At 1020, the process 1000 continues with providing a properly sized nasal packing device 10, 900 (such as one with the dimensions discussed previously for the tube 12 and bags 30, 40, and 940 or with smaller dimensions, such as for children, that still has a surface area defining a volume larger than the two nasal cavities 50, 60).

At 1024, the exterior surfaces of the bags 30, 40, and 940 are pretreated to enhance the functioning of the device 10, 900. For example, testing of the embodiment of the device 900 shown in FIG. 9 has indicated that adding a lubricant (e.g., K-Y™ Jelly or other lubricant) allowed the bags 30, 940 to not only fill the nasal cavities 50, 60 (as occurs without lubrication) but to overcome surface tension or resistances to fully fill and then inflate into the recesses of the turbinates 55 with sufficient pressure to control epistaxis. Additionally, re-bleeds caused by blood adherence to a packing device can be problematic. To address blood adherence, step 1024 may include (in addition to using a material, such as polyurethane, that reduces adherence) treating the exterior surfaces of the bag 30, 40, and 940 to reduce adherence. One embodiment of the process 1000 includes ionization of the bag surfaces (e.g., ionized polyurethane) to control blood adherence and reduce re-bleeding upon deflation and removal of the device 10, 900. The surfaces may further be treated with substances to promote hemostasis and/or antibacterial/antiviral activity. Step 1024 (or portions of step 1024) may be performed immediately prior to insertion but typically are performed in advance with the device 10, 900 being stored in a ready-to-use state, e.g., after steps 1010, 1020, and 1024.

At 1030, a patient is experiencing epistaxis and the device 10, 900 is inserted into the nasal passages of the epistaxis patient (see, for example, FIG. 6). The bags 30, 40, 940 are typically fully (or substantially) deflated to allow easy insertion, and also the air or gas supply tubes 36, 46 have been inserted into the openings in the two fill lumens or catheters 32, 42. After insertion in 1030, the source (not shown) to be used for filling and pressurizing the bags 30, 40, 940 is attached to the one-way valves 38, 48. The source preferably includes device for measuring pressures in the bags 30, 40, 940 although this is not necessary. The pressure measurement device is useful for assuring that filling of the bags 30, 40, 940 is performed at a low pressure to provide proper positioning (complying) of the bags 30, 40, 940 with minimal pain and discomfort for the epistaxis patient and then for assuring that adequate inflation pressure is achieved to apply force with the exterior surfaces of the bags 30, 40, 940 against the nasal wall tissues to stop or control bleeding.

At 1038, the posterior bag 40, 940 is filled with gas, such as air, or other fluid at a relatively low fill pressure. This lower pressure allows the bag 40, 940 to slowly and gently expand toward its oversized volume and to conform to the irregular contours of the posterior nasal cavity and nasopharynx 60. Concurrently or sequentially, step 1040 is performed to initially fill the anterior bag 30 with low fill pressure gas, again the low pressure gas, such as air, causes the bag 30 surfaces to gently conform to the contours and shape of the anterior nasal cavity 50 including the turbinates 55 (and if present, irregularities caused by a deviated septum 70). The fill pressure typically is very low, such as less than about 20 mmHg but can be higher such as between 20 and 60 mmHg or higher to complete steps 1038 and 1040 with minimal discomfort to the patient.

At 1050, the gas source is further operated to increase the pressure within the posterior bag 40, 940 to a pressure useful for controlling or stopping epistaxis in the posterior nasal cavity and nasopharynx 60. Typically, this second or inflation pressure is significantly higher than the fill pressure and typically is based on the applying a force equal to or greater than the intranasal arterial pressure, which is generally about 80 mmHg. In one embodiment, the second or inflation pressure applied at 1050 is greater than about 60 mmHg and more preferably greater than about 80 mmHg to better control or stop bleeding. At 1060, concurrent with or after 1050, the gas source is operated to increase the pressure within the anterior bag 30 to the second or inflation pressure (sometimes also called the bleeding control pressure). At 1064, the higher inflation pressure is maintained for a period of time to allow sufficient clotting to stop bleeding or left in place to control bleeding. Typically, between 50 and 100 seconds or more, and in one embodiment, bleeding is stopped at about 65 seconds. At 1070, the bags 30, 40, 940 are deflated such as by opening valves 38, 48 or removing tubes 36, 46. Finally, at 1080, the device 10, 900 is removed from the patient's nasal passages.

The above disclosure sets forth a number of embodiments of the present invention. Other arrangements or embodiments, not precisely set forth, could be practiced under the teachings of the present invention and as set forth in the following claims. For example, additional treatments could be applied to the external bag wall which would promote hemostasis or antibacterial/antiviral activity. Further, internal bag treatments could be applied for the purpose of decreasing friction, antibacterial/antiviral activity, or automatic sealing of a bag leak. Also, ionization of the bag could lessen the tendency for clot to adhere to the bag. The bag(s) could be bivalved in order to pass around a very prominent septal spur. Further, the above description stresses the use of two oversized bags made of non-elastic material, but the inventor understands that two or more bags may be utilized to practice the invention and devices having three, four, or even more oversized bags are considered within the breadth of the invention with understanding of the above description.

I claim:

1. An inflatable apparatus for insertion into a nasal passage of a patient for controlling epistaxis, comprising:
   an insertion tube having a first inlet for receiving gas or fluid from a first source and a first outlet for the gas or fluid received from the first source and a second inlet for receiving gas or fluid from a second source and a second outlet for the gas or fluid received from the second source;
   a first bag including sealed sidewalls comprising non-elastic material sealably connected to the insertion tube with a fully-inflated interior volume defined by the bag sidewalls and in fluid communication with the first outlet, wherein the exterior of the first bag has a flat surface and the interior volume of the first bag defined by the sidewalls is greater than the volume of the anterior nasal cavity of the patient; and
   a second bag including sealed sidewalls comprising non-elastic material sealably connected to the insertion tube with a fully-inflated interior volume defined by the bag sidewalls and in fluid communication with the second outlet, wherein said second bag partially overlaps with said first bag and the exterior of the second bag has a flat surface and the interior volume of the second bag defined by the sidewalls is greater than the volume of the posterior nasal cavity and nasopharynx of the patient.

2. The apparatus of claim 1, wherein the insertion tube comprises a lumen providing a passageway through the insertion tube.

3. The apparatus of claim 1, wherein the interior volume of the first bag defined by the sidewalls is greater than about 24 cubic centimeters and the interior volume of the second bag defined by the sidewalls is greater than about 10 cubic centimeters.

4. The apparatus of claim 1, wherein the first bag is connected to the insertion tube by a pair of seals at spaced apart first and second locations along the length of the insertion tube.

5. The apparatus of claim 4, wherein the second bag is connected to the insertion tube by a pair of seals at spaced apart third and fourth locations along the length of the insertion tube, the second and third locations being substantially adjacent.

6. The apparatus of claim 4, wherein the second bag is connected to the insertion tube by a pair of seals at spaced apart third and fourth locations along the length of the insertion tube, the third location being more proximate to the first location than the second location such that the first and second bags overlap for a length measured along a longitudinal axis of the insertion tube.

7. The apparatus of claim 6, the length being greater than about 0.25 inches.

8. The apparatus of claim 1, further including a layer of lubrication on an exterior surface of the sidewalls of the first and second bags.

9. The device of claim 8, further including a first pressurized fill source connected to the inlet to the first fill lumen and a second pressurized fill source connected to the inlet to the second fill lumen, wherein the first and second pressurized fill sources are independently operable.

10. The device of claim 9, wherein the first and second pressurized gas sources are operable to provide pressurized gas or fluid at a fill pressure to fill the first and second bags and at an inflation pressure higher than the fill pressure to pressurize the first and second bags to an epistaxis control pressure.

11. The device of claim 10, wherein the epistaxis control pressure is greater than about 60 millimeters Hg.

12. The apparatus of claim 1, wherein the non-elastic material of the sidewalls of the first and second bags is treated with ionization.

13. An inflatable nasal packing device, comprising:

an insertion tube comprising three lumen including an air passageway lumen extending the length of the tube with an opening at each end of the tube, a first fill lumen with an inlet at one end of the tube and an outlet in a first portion of the tube, and a second fill lumen with an inlet adjacent the inlet for the first fill lumen and an outlet in a second portion of the tube;

a first bag formed of non-elastic, flexible material positioned about the first portion of the tube and sealed to the tube with a pair of circumferential end seals that are spaced apart on the tube such that the first bag encloses a first portion of the tube; and a second bag formed of non-elastic, flexible material positioned about the second portion of the tube and sealed to the tube with a pair of circumferential end seals that are spaced apart on the tube such that the second bag encloses a second portion of the tube wherein said first and second bag have flat outer surfaces that partially overlap one another.

14. The device of claim 13, wherein the first and second portions overlap for a length of the tube as measured along a longitudinal axis of the tube.

15. The device of claim 13, wherein the first bag comprises a first wall and a second wall that have a substantially fixed surface area, the first and second walls of the first bag defining an interior volume greater than about 16 cubic centimeters and further wherein the second bag comprises a first wall and a second wall that have a substantially fixed surface area, the first and second walls of the second bag defining an interior volume greater than about 10 cubic centimeters.

16. The device of claim 13, wherein the material of the first and second bags is polyurethane and wherein external surfaces of the first and second bags are lubricated.

* * * * *